United States Patent [19]

Weichert et al.

[11] Patent Number: 5,670,544

[45] Date of Patent: Sep. 23, 1997

[54] SUBSTITUTED BENZOYLGUANIDINES PROCESS FOR THEIR PREPARATION THEIR USE AS A MEDICAMENT OR DIAGNOSTIC AND MEDICAMENT CONTAINING THEM

[75] Inventors: Andreas Weichert, Frankfurt; Hans-Jochen Lang, Hofheim; Heinz-Werner Kleemann, Bad Homburg; Wolfgang Scholz, Eschborn; Udo Albus, Florstadt, all of Germany

[73] Assignee: Hoechst Aktiengesellschaft, Frankfurt am Main, Germany

[21] Appl. No.: 451,310

[22] Filed: May 26, 1995

Related U.S. Application Data

[63] Continuation of Ser. No. 337,237, Nov. 4, 1994, abandoned, which is a continuation of Ser. No. 165,667, Dec. 13, 1993, abandoned.

[30] Foreign Application Priority Data

Dec. 1, 1959 [DE] Germany .......................... 42 42 192.6

[51] Int. Cl.$^6$ .................... A61K 31/165; C07C 233/34
[52] U.S. Cl. .................... 514/618; 514/614; 514/617; 514/634; 564/147; 564/237; 564/86; 564/88; 564/89
[58] Field of Search .......................... 562/429; 564/147; 564/237, 86, 88, 89; 514/634, 614, 602, 603, 604, 617, 618

[56] References Cited

U.S. PATENT DOCUMENTS

| | | | |
|---|---|---|---|
| 3,780,027 | 12/1973 | Cragoe, Jr. et al. | 260/239.6 |
| 5,091,394 | 2/1992 | Englert et al. | 514/331 |

FOREIGN PATENT DOCUMENTS

| | | | |
|---|---|---|---|
| 0 416 499 A3 | 3/1991 | European Pat. Off. | |
| 1939738 | 2/1971 | Germany | 514/634 |
| 2032425 | 5/1980 | United Kingdom | 514/634 |

*Primary Examiner*—Shailendra Kumar
*Attorney, Agent, or Firm*—Finnegan, Henderson, Farabow, Garrett & Dunner, L.L.P.

[57] ABSTRACT

There are described benzoylguanidines of the formula I

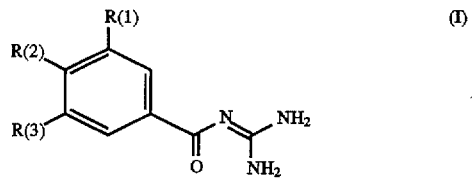

where

R(1) is hydrogen, Hal, —NO$_2$, —CN, —CF$_3$, R(4)—SO$_m$ or R(5)R(6)N—SO$_2$—, where m is zero to 2, R(4) and R(5) are alk(en)yl or —C$_n$H$_{2n}$—R(7), n is zero to 4, where R(5) also has the meaning of H, R(6) is H or (C$_1$–C$_4$)-alkyl, where R(5) and R(6) together can be 4 or 5 methylene groups, R(2) is —SR(10), —OR(10), —NRH(10), —NR(10)R(11), —CHR(10)R(12),

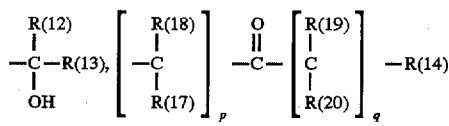

where R(10) and R(11) are identical or different and are
—[CHR(16)]$_s$—(CH$_2$)$_p$—(CHOH)$_q$—(CH$_2$)$_r$—(CH$_2$OH)$_t$,
—R(21) or —(CH$_2$)$_p$—O—(CH$_2$—CH$_2$O)$_q$—R(21)

R(12) and R(13) are hydrogen or alkyl or, together with the carbon atom carrying them, form a cycloalkyl, R(14) is H, (cyclo)alkyl or —C$_n$H$_{2n}$—R(15), R(3) is defined as R(1), or is alkyl, hydrogen or —X—R(22) where X is oxygen, S or NR(16), and their pharmaceutically tolerable salts.

The compounds I have very good antiarrhythmic properties, but not undesired salidiuretic properties. Moreover, they are distinguished by strong inhibitory action on the proliferation of cells.

3 Claims, No Drawings

SUBSTITUTED BENZOYLGUANIDINES PROCESS FOR THEIR PREPARATION THEIR USE AS A MEDICAMENT OR DIAGNOSTIC AND MEDICAMENT CONTAINING THEM

This application is a continuation of prior application Ser. No. 08/337,237 filed Nov. 4, 1994, now abandoned which is a continuation of first-filed application Ser. No. 08/165,667 filed Dec. 13, 1993, now abandoned.

The invention relates to benzoylguanidines of the formula I

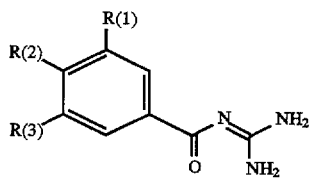

in which:

R(1) is hydrogen, F, Cl, Br, I, —$NO_2$, —C≡N, —$CF_3$, R(4)—$SO_m$ or R(5)R(6)N—$SO_2$—,
m is zero, 1 or 2,
R(4) and R(5) are ($C_1$–$C_8$)-alkyl, ($C_3$–$C_6$)-alkenyl, —$C_nH_{2n}$—R(7) or $CF_3$,
n is zero, 1, 2, 3 or 4,
R(7) is ($C_3$–$C_7$)-cycloalkyl or phenyl which is unsubstituted or substituted by 1–3 substituents from the group comprising F, Cl, $CF_3$, methyl, methoxy and NR(8)R(9) where
R(8) and R(9) are H or ($C_1$–$C_4$)-alkyl,
where R(5) also has the meaning of H,
R(6) is H or ($C_1$–$C_4$)-alkyl,
where R(5) and R(6) together can be 4 or 5 methylene groups, of which one $CH_2$ group can be replaced by Oxygen, S, NH, N—$CH_3$ or N-benzyl,
R(2)=—SR(10), —OR(10), —NHR(10), —NR(10)R(11), —CHR(10)R(12),

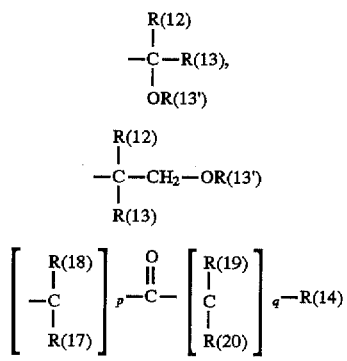

R(10) and R(11) are identical or different —[CHR(16)]$_s$—($CH_2$)$_p$—(CHOH)$_q$—($CH_2$)$_r$—(CHOH)$_r$—R(21)—($CH_2$)$_p$—O—($CH_2$—$CH_2$O)$_q$—R(21),
R(21) is hydrogen or methyl,
p, q and r are identical or different zero, 1, 2, 3 or 4,
s is zero or 1,
t is 1, 2, 3 or 4,
R(12) and R(13) are identical or different hydrogen, ($C_1$–$C_6$)-alkyl or, together with the carbon atom carrying them, are a ($C_3$–$C_8$)-cycloalkyl,
R(13') is hydrogen or ($C_1$–$C_4$)-alkyl,
R(14) is H, ($C_1$–$C_6$)-alkyl, ($C_3$–$C_8$)-cylcoalkyl or —$C_aH_{2a}$—R(15), a is zero, 1, 2, 3 or 4,
R(15) is phenyl which is unsubstituted or substituted by 1–3 substituents from the group comprising F, Cl, $CF_3$, methyl, methoxy and NR(8)R(9) where R(8) and R(9) are H or ($C_1$–$C_4$)-alkyl,
($C_1$–$C_9$)-heteroaryl, which is unsubstituted or substituted as phenyl,
($C_1$–$C_6$)-alkyl, which is unsubsituted or substituted by 1–3 OH,
R(16), R(17), R(18), R(19) and R(20) are hydrogen or ($C_1$–$C_3$)-alkyl,
R(3) is defined as R(1), or is ($C_1$–$C_6$)-alkyl or —X—R(22),
X is oxygen, S or NR(16),
R(16) is H, ($C_1$–$C_3$)-alkyl,
where R(22) and R(16) together can also be 4 or 5 methylene groups and one $CH_2$ group can be replaced by oxygen, S, NH, N—$CH_3$ or N-benzyl,
R(22) is defined as R(14);
and their pharmaceutically tolerable salts.

Preferred compounds I are those in which:
R(1) is hydrogen, F, Cl, —C≡N, —$CF_3$, R(4)—$SO_m$ or R(5)R(6)N—$SO_2$—, where
m is zero, 1 or 2,
R(4) and R(5) are ($C_1$–$C_8$)-alkyl, ($C_3$–$C_4$)-alkenyl, —$C_nH_{2n}$—R(7) or —$CF_3$,
n is zero or 1,
R(7) is ($C_3$–$C_6$)-cycloalkyl or phenyl
which is unsubstituted or substituted by 1–3 subsituents from the group comprising F, Cl, $CF_3$, methyl, methoxy and NR(8)R(9) where
R(8) and R(9) are H or methyl, where R(5) also has the meaning of H,
R(6) is H or methyl,
R(3) is hydrogen, methyl, cyano, or F, Cl, —$CF_3$ and the other radicals are as defined above,
and their pharmaceutically tolerable salts.

Particularly preferred compounds I are those in which:
R(1) is F, Cl, —C≡N, —$CF_3$, R(4)—$SO_m$ or R(5)R(6)N—$SO_2$—,
m is zero, 1 or 2,
R(4) is methyl or —$CF_3$,
R(5) and R(6) independently of one another are H or methyl;
R(2)=—SR(10), —OR(10), NHR(10), —NR(10)R(11), —CHR(10)R(12),

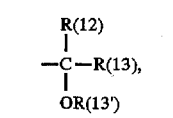

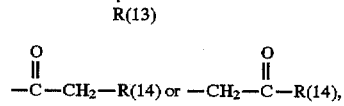

R(10) and R(11) are identical or different —$CH_2$—(CHOH)$_q$—CHOH—CHOH—CHOH—$CH_2$OH, —$CH_2$—CHOH—$CH_2$OH, —[CHR(16)]$_s$—$CH_2$—CHOH—R(21) or —($CH_2$)$_p$—O—($CH_2$—$CH_2$—O)$_q$—$CH_3$,
p is zero, 1 or 2,
q is zero, 1 or 2, s is zero or 1, R(21) is hydrogen or methyl, R(12) and R(13) are identical or different hydrogen, methyl or, together with the carbon atom carrying them, a $(C_3-C_8)$-cycloalkyl, R(13') is hydrogen or methyl, R(14) is H, $(C_1-C_6)$-alkyl, $(C_3-C_8)$-cycloalkyl, $—C_aH_{2a}—R(15)$ , a is 0 or 1, R(15) is phenyl,
which is unsubstituted or substituted by 1-2 radicals from the series comprising F, Cl, $CF_3$ and $—CH_3$, or heteroaryl from the series comprising furanyl thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl and pyridazinyl, which are unsubstituted or substituted by a radical from the series comprising F, Cl, $CF_3$ and $—CH_3$, $(C_1-C_4)$-alkyl which is substituted by an OH;

R(16) is hydrogen or methyl,

R(3) is methyl, cyano, trifluoromethyl, F, Cl or hydrogen, and their pharmaceutically tolerable salts.

Very particularly preferred compounds are those where R(15) is phenyl,
which is unsubstituted or substituted by 1-2 radicals from the series comprising F, Cl and $CF_3$,
imidazolyl, tetrazolyl, pyridinyl or pyrimidinyl,
which are unsubstituted or substituted by a radical from the series comprising F, Cl, $CF_3$ and $CH_3$.

$(C_1-C_9)$-heteroaryl is understood in particular as meaning radicals which are derived from phenyl or naphthyl, in which one or more CH groups are replaced by N and/or in which at least two adjacent CH groups are replaced (with formation of a 5-membered aromatic ring) by S, NH or O.

In addition, one or both atoms of the condensation site of bicyclic radicals (such as in indolizinyl) can also be nitrogen atoms.

Heteroaryl is in particular furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl.

If one of the substituents R(1) to R(22) contains one or more centers of asymmetry, this can have either the S or R configuration. The compounds can be present as optical isomers, as diastereomers, as racemates or as mixtures thereof.

The designated alkyl radicals can be present either in straight-chain or branched form.

The invention furthermore relates to a process for the preparation of the compounds I, which comprises reacting compounds of the formula II

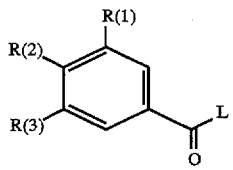

(II)

in which R(1) to R(3) have the given meaning and L is a leaving group which can be easily nucleophilically substituted with guanidine.

The activated acid derivatives of the formula II in which L is an alkoxy group, preferably a methoxy group, a phenoxy group, a phenylthio, methylthio or 2-pyridylthio group, or a nitrogen heterocycle, preferably 1-imidazolyl, are advantageously obtained in a manner known per se from the carbonyl chlorides (formula II, L≡Cl) on which they are based, which for their part can in tun be prepared in a manner known per se from the carboxylic acids (formula II, L≡OH) on which they are based, for example using thionyl chloride.

In addition to the carbonyl chlorides of the formula II (L≡Cl), other activated acid derivatives of the formula II can also be prepared in a manner known per se directly from the benzoic acid derivatives (formula II, L≡OH) on which they are based, such as, for example, the methyl esters of the formula II where L≡OCH$_3$ by treatment with gaseous HCl in methanol, the imidazolides of the formula II by treatment with carbonyldiimidazole [L≡1-imidazolyl, Staab, Angew. Chem. Int. Ed. Engl. 1, 351–367 (1962)], the mixed anhydrides II using Cl—COOC$_2$H$_5$ or tosyl chloride in the presence of triethylamine in an inert solvent, and also the activation of benzoic acids using dicyclohexylcarbodiimide (DCC) or using O-[(cyano(ethoxycarbonyl)methylene) amino]-1,1,3,3-tetramethyluronium tetrafluoborate ("TOTU") [Weiss and Krommer, Chemiker Zeitung 98, 817 (1974)]. A number of suitable methods for the preparation of activated carboxylic acid derivatives of the formula II are given under details of source literature in J. March, Advanced Organic Chemistry, Third Edition (John Wiley & Sons, 1985), p. 350.

The reaction of an activated carboxylic acid derivative of the formula I with guanidine is carried out in a manner known per se in a protic or aprotic polar but inert organic solvent. Methanol, isopropanol or THF between 20° C. and the boiling point of these solvents have proven suitable in the reaction of the methyl benzoates (II, L≡OMe) with guanidine. In most reactions of compounds II with salt-free guanidine, the reaction was advantageously carried out in aprotic inert solvents such as THF, dimethoxyethane or dioxane. However, water can also be used as a solvent in the reaction of II and III if a base such as, for example, NaOH is used.

If L≡Cl the reaction is advantageously carried out with the addition of an acid scavenger, for example in the form of excess guanidine for binding the hydrohalic acid.

Some of the underlying benzoic acid derivatives of the formula II are known and described in the literature. The unknown compounds of the formula II can be prepared by methods known from the literature, by converting, for example, 4-(or 5-)halo-3-chlorosulfonylbenzoic acids into 3-aminosulfonyl-4-(or 5-)halobenzoic acids with ammonia or amines or into 3-alkylsulfonyl-4-(or 5-)halobenzoic acids with a weak reductant such as sodium bisulfite and subsequent alkylation, and reacting the resulting benzoic acids according to one of the process variants described above to give compounds I according to the invention. The introduction of some substituents in the 4- and 5-position is carried out by methods known from the literature of palladium-mediated cross-coupling of aryl halides with, for example, organostannanes, organoboronic acids or organoboranes or organocopper or zinc compounds.

In general, benzoylguanidines I are weak bases and can bind acid with the formation of salts. Possible acid addition salts are salts of all pharmacologically tolerable acids, for example halides, in particular hydrochlorides, lactates, sulfates, citrates, tartrates, acetates, phosphates, methanesulfonates and p-toluenesulfonates.

The compounds I are substituted acylguanidines. The most prominent representative of the acylguanidines is the pyrazine derivative amiloride, which is used in therapy as a potassium-sparing diuretic. Numerous other compounds of the amiloride type are described in the literature, such as, for example, dimethylamiloride or ethylisopropylamiloride.

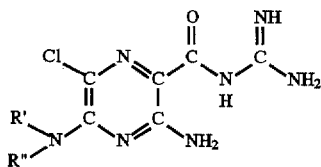

Amiloride: R', R"≡H

Dimethylamiloride: R', R"≡CH$_3$

Ethylisopropylamiloride: R'≡C$_2$H$_5$, R"≡CH(CH$_3$)$_2$

Investigations have moreover been disclosed which point to antiarrhythmic properties of amiloride [Circulation 79, 1257–63 (1989)]. Obstacles to wide use as an antiarrhythmic are, however, that this effect is only slightly pronounced and occurs accompanied by a hypotensive and saluretic action and these side effects are undesired in the treatment of cardiac arrhythmias.

Indications of antiarrhythmic properties of amiloride were also obtained in experiments on isolated animal hearts [Eur. Heart J. 9 (suppl. 1): 167 (1988)] (book of abstracts). For instance, it was found in rat hearts that an artificially induced ventricular fibrillation could be suppressed completely by amiloride. The above mentioned amiloride derivative ethylisopropylamiloride was even more potent than amiloride in this model.

U.S. Pat. No. 5,091,394 (HOE 89/F 288) describes benzoylguanidines which carry a hydrogen atom in the position corresponding to the radical R(1). German Patent Application P 42 04 575.4 (HOE 92/F 034) proposes 3,5-substituted benzoylguanidines in which, however, the substituents R(2) and R(3) do not have the meanings claimed according to the present invention.

In U.S. Pat. No. 3,780,027, acylguanidines are claimed which are structurally similar to the compounds of the formula I and are derived from commercially available loop diuretics, such as bumetanide. A strong salidiuretic activity is correspondingly reported for these compounds.

It was therefore surprising that the compounds according to the invention have no undesired and disadvantageous salidiuretic properties, but very good antiarrhythmic properties, as occur, for example, in the case of oxygen deficiency symptoms. As a result of their pharmacological properties, the compounds are outstandingly suitable as antiarrhythmic pharmaceuticals having a cardioprotective component for infarct prophylaxis and infarct treatment and for the treatment of angina pectoris, where they also preventively inhibit or greatly decrease the pathophysiological processes in the formation of ischemically induced damage, in particular in the production of ischemically induced cardiac arrhythmias. Because of their protective actions against pathological hypoxic and ischemic situations, the compounds of the formula I according to the invention can be used as a result of inhibition of the cellular Na$^+$/H$^+$ exchange mechanism as pharmaceuticals for the treatment of all acute or chronic damage caused by ischemia or primary or secondary diseases induced thereby. This relates to their use as pharmaceuticals for surgical interventions, for example in organ transplantation, where the compounds can be used both for the protection of the organs in the donor before and during removal, for the protection of removed organs, for example during treatment with or storage thereof in physiological bath fluids, and during transfer to the body of the recipient. The compounds are also useful protective pharmaceuticals during the performance of angioplastic surgical interventions, for example in the heart and in peripheral vessels. In accordance with their protective action against ischemically induced damage, the compounds are also suitable as pharmaceuticals for the treatment of ischemias of the nervous system, in particular the CNS, where they are suitable, for example, for the treatment of stroke or of cerebral edema. Moreover the compounds of the formula I according to the invention are also suitable for the treatment of forms of shock, such as, for example, allergic, cardiogenic, hypovolemic and bacterial shock.

Moreover, the compounds of the formula I according to the invention are distinguished by potent inhibitory action on the proliferation of cells, for example fibroblast cell proliferation and the proliferation of smooth muscle cells. The compounds of the formula I can therefore be considered as useful therapeutics for diseases in which cell proliferation is a primary or secondary cause, and can therefore be used as antiatherosclerotics, agents against diabetic late complications, cancers, fibrotic diseases such as pulmonary fibrosis, fibrosis of the liver or fibrosis of the kidneys, organ hypertrophies and hyperplasias, in particular in prostate hyperplasia or prostate hypertrophy.

The compounds according to the invention are active inhibitors of the cellular sodium-proton antiporter (Na$^+$/H$^+$ exchanger), which is raised in numerous diseases (essential hypertension, atherosclerosis, diabetes, etc.) even in those cells which are easily accessible to measurements, such as, for example, in erythrocytes, platelets or leucocytes. The compounds according to the invention are therefore suitable as excellent and simple scientific tools, for example in their use as diagnostics for the determination and differentiation of certain forms of hypertension, but also of atherosclerosis diabetes, proliferative diseases etc. Moreover, the compounds of the formula I are suitable for preventive therapy for the prevention of the formation of high blood pressure, for example, essential hypertension.

Compared to the known compounds, the compounds according to the invention have a significantly improved water solubility. They are therefore significantly more highly suitable for i.V. administration.

Pharmaceuticals which contain a compound I can be administered orally, parenterally, intravenously, rectally or by inhalation, the preferred administration being dependent on the particular type of the disease. The compounds I can be used on their own or together with pharmaceutical auxiliaries, to be precise both in veterinary and in human medicine.

The auxiliaries which are suitable for the desired pharmaceutical formulation are familiar to the person skilled in the art on the basis of his knowledge. In addition to solvents, gelling agents, suppository bases, tabletting auxiliaries and other active compound excipients, antioxidants, dispersants, emulsifiers, antifoams, flavor correctants, preservatives, solubilizers or colorants, for example, can be used.

For a form for oral administration, the active compounds are mixed with the additives suitable for this purpose, such as excipients, stabilizers or inert diluents, and are brought by the customary methods into the suitable administration forms, such as tablets, coated tablets, hard gelatine capsules, or aqueous, alcoholic or oily solutions. Inert excipients which can be used are, for example, gum arabic, magnesia, magnesium carbonate, potassium phosphate, lactose, glucose or starch, in particular cornstarch. Preparation can be carried out here both as dry and as moist granules. Suitable oily excipients or solvents are, for example, vegetable or animal oils, such as sunflower oil or fish liver oil.

For subcutaneous or intravenous administration, the active compounds are brought into solution, suspension or emulsion, if desired using the substances customary for this purpose such as solubilizers, emulsifiers or other auxiliaries. Suitable solvents are, for example water, physiological saline solution or alcohols, for example ethanol, propanol, glycerol, and also sugar solutions such as glucose or mannitol solutions, or alternatively a mixture of the various solvents mentioned.

Pharmaceutical formulations suitable for administration in the form of aerosols or sprays are, for example, solutions, suspensions or emulsions of the active compound of the formula I in a pharmaceutically acceptable solvent, such as, in particular, ethanol or water, or a mixture of these solvents.

If required, the formulation can also contain still other pharmaceutical auxiliaries such as surfactants, emulsifiers and stabilizers as well as a propellant gas. Such a preparation contains the active compound customarily in a concentration from about 0.1 to 10, in particular from about 0.3 to 3% by weight.

The dose of the active compound of the formula I to be administered and the frequency of administration depend on the potency and duration of action of the compounds used and additionally on the type and severity of the disease to be treated and on the sex, age, weight and individual responsiveness of the mammal to be treated. On average, the daily dose of a compound of the formula I in a patient of weight about 75 kg is at least 0.001 mg/kg, preferably 0.01 mg/hg, to at most 10 mg/kg, preferably 1 mg/kg of body weight. In acute episodes of the disease, for example immediately after suffering a cardiac infarct, even higher and in particular more frequent doses may be necessary, for example up to 4 individual doses per day. In particular when administered i.v., for example in the case of an infarct patient in the intensive care unit, up to 200 mg per day may be necessary.

| List of abbreviations: | |
|---|---|
| MeOH | methanol |
| DMF | N,N-dimethylformamide |
| NBS | N-bromosuccinimide |
| AIBN | α,α-azobisisobutyronitrile |
| EI | electron impact |
| DCI | desorption-chemical ionization |
| RT | room temperature |
| EA | ethyl acetate (EtOAc) |
| DIP | diisopropyl ether |
| MTB | methyl tertiary butyl ether |
| mp | melting point |
| HEP | n-heptane |
| DME | dimethoxyethane |
| FAB | fast atom bombardment |
| CH$_2$Cl$_2$ | dichloromethane |
| THF | tetrahydrofuran |
| eq | equivalent |

Experimental Section

General Procedure for the preparation of benzoylguanidines (I)

Variant A: from benzoic acids (II, L≡OH) 0.01 mol of the benzoic acid derivative of the formula II is dissolved or suspended in 60 ml of anhydrous THF and then treated with 1.78 g (0.011 mol) of carbonyldiimidazole. After stirring for 2 hours at room temperature, 2.95 g (0.05 mol) of guanidine are introduced into the reaction solution. After stirring overnight, the THF is distilled off under reduced pressure (Rotavapor), the residue is treated with water, the mixture is adjusted to pH 6–7 with 2N HCL and the corresponding benzoylguanidine (formula I) is filtered off. The benzoylguanidines thus obtained can be converted into the corresponding salts by treatment with treatment with aqueous or methanolic or ethereal hydrochloric acid or other pharmacologically tolerable acids.

General procedure for the preparation of benzoylguanidines (I)

Variant B: from alkyl benzoate (II, L≡O-alkyl) 5 mmol of the alkyl benzoate of the formula II and 25 mmol of guanidine (free base) are dissolved in 15 ml of isopropanol or suspended in 15 ml of THF and boiled under reflux (typical reaction time 2 to 5 h) until conversion is complete (thin-layer checking). The solvent is removed by distillation under reduced pressure (Rotavapor), the residue is taken up in 300 ml of EA and the solution is washed three times with 50 ml of NaHCO$_3$ solution each time. It is dried over Na$_2$SO$_4$, the solvent is removed by distillation in vacuo and the residue is chromatographed on silica gel using a suitable eluent, e.g. EA/MeOH 5:1. (For salt formation see Variant A).

EXAMPLE 1

4-(1'-Hydroxy-1'-methyl)ethyl-3-methylsulfonyl-benzoylguanidine hydrochloride

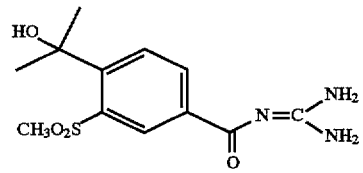

Synthesis route:

a) Oxidation of methyl 4-ethyl-3-methylsulfonylbenzoate to give methyl 4-acetyl-3-methylsulfonylbenzoate in glacial acetic acid using KMnO$_4$/benzyltriethylammonium permanganate (2:1 eq) at RT for two days, extract with EA after addition of water and NaHCO$_3$ and dry org. phase (MgSO$_4$), triturate in ethanol, filter off colorless crystals, mp 111° C.

b) Add methyl 4-(1'-hydroxy-1'-methyl)ethyl-3-methylsulfonylbenzoate from a) in methylene chloride to a solution of 2 eq of dimethylzinc and 2 eq of TiCl$_4$ at −20° C. and allow to warm to RT during the course of 3 hours, pour the mixture into water, extract by shaking with CH$_2$Cl$_2$, dry (MgSO$_4$) and remove solvent in vacuo. Colorless crystals, mp 133° to 135° C.

c) 4-(1'-Hydroxy-1'-methyl)ethyl-3-methylsulfonylbenzoylguanidine hydrochloride from b) according to general procedure B (see above). Colorless crystals, mp 219° to 220° C.

EXAMPLE 2

4-(2-Methoxyethoxy)methoxy-3-methylsulfonylbenzoylguanidine

Methanesulfonic acid salt

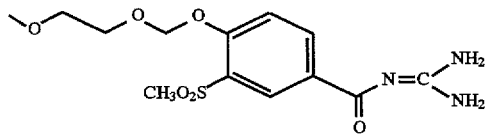

Synthesis route:

a) Methyl 4-hydroxy-3-methylsulfonylbenzoate 6 mmol of methyl 4-chloro-3-methylsulfonylbenzoate and 6 mmol of H$_2$O are dissolved in 30 ml of tetramethylurea, 18 mmol of K$_2$CO$_3$ are then added, and the mixture is then stirred at 130° C. for 2 h. The cooled reaction mixture is poured into 100 ml of saturated aqueous $NaHCO_3$ solution and extracted 5 times using 100 ml of EA each time. The extracts are dried over $Na_2SO_4$, the solvent is removed in vacuo and the residue is chromatographed on silica gel using EA.

$R_f(EA)=0.36$ MS(DCI): 231 (M+1)

b) Methyl 4-(2-methoxyethoxy)methoxy-3-methylsulfonylbenzoate 2.2 mmol of the phenol from 2a) and 4.4 mmol of ethyldiisopropylamine are dissolved in 10 ml of $CH_2Cl_2$, and 3.3 mmol of (2-methoxyethoxy)methyl chloride are then added at RT. The mixture is stirred at RT for 3 days, then the solvent is removed in vacuo, and the residue is taken up in 100 ml of EA. The solution is washed three times with 50 ml of 0.3M $KH_2PO_4$ each time, then twice with 50 ml of $Na_2CO_3$ each time. It is dried over $Na_2SO_4$, the solvent is removed in vacuo, and the substance is further employed without additional purification.

$R_f(EA)=0.45$ MS(DCI): 319 (M+1)

c) The title compound of Example 2 is obtained from b) according to general procedure B. The free base is dissolved in MeOH and treated with one equivalent of methanesulfonic acid. The salt is precipitated using DIP and filtered off with suction.

Colorless crystals, mp 167° C. MS(DCI): 346(M+1)

EXAMPLE 3

4-[2(R),3(R),4(R),5(R),6-Pentahydroxyhexylamino]-3-methylsulfonylbenzoylguanidine hydrochloride

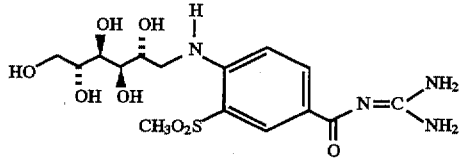

Synthesis route:

a) N-benzhydryl-N-[2(R),3(R),4(R),4(R),6-pentahydroxyhexyl]amine 2,3:5,6-diacetonide 24 mmol of N-benzhydrylmannofuranosylamine 2,3:5,6-diacetonide (J. Med. Chem. 1992, 35, 559) are dissolved in 150 ml of THF and treated with 60 mmol of $LiAlH_4$ in portions at RT. The mixture is stirred at RT for 2 h, then poured into 250 ml of $NaHCO_3$ solution and extracted 3 times using 200 ml of EA each time. The extracts are dried over $Na_2SO_4$, the solvent is removed in vacuo and the residue is further employed without additional purification. Colorless oil.

$R_f$ (DIP)=0.33 MS(FAB): 428 (M+1)

b) [2(R),3(R),(4)R,5(R),6-Pentahydroxyhexyl]amine 2,3:5,6-diacetonide 24 mmol of the compound 3a) are dissolved in 200 ml of MeOH and treated with 240 mmol of ammonium formate and 2 g of Pd/C and the mixture is stirred at RT for 4 h. The mixture is filtered off and the solvent is removed in vacuo; the residue is then taken up in 100 ml of EA/100 ml of $Na_2CO_3$ solution. The solution is extracted a further two times using 200 ml of EA each time and dried over $Na_2SO_4$, and the solvent is removed in vacuo. The residue is chromatographed on silica gel using EA/MeOH 1:1. Colorless oil.

$R_f$ (EA/MeOH 1:1)=0.2 MS(DCI): 262 (M+1)

c) 4-[2(R),3(R),4(R),5(R),6-Pentahydroxyhexylemino]-3-methylsulfonylbenzoic acid 2,3:5,6-diacetonide 2.3 mmol of the amine from 3b), 2.3 mmol of 4-fluoro-3-methylsulfonylbenzoic acid and 4.6 mmol of diisopropylethylamine are dissolved in 10 ml of tetramethylurea and the mixture is stirred at 120° C. for 3 h. The solvent is then removed in vacuo, and the residue is chromatographed on silica gel using EA/MeOH 10:1. A light-brown oil is obtained. $R_f$ (EA/MeOH 5:1)=0.5 MS(FAB): 460 (M+1)

d) 4-[2(R),3(R),4(R),5(R),6-Pentahydroxyhexylamino]-3-methylsulfonylbenzoylguanidine 2,3:5,6-diacetonide 2 mmol of the benzoic acid 2c) are reacted according to general procedure A and the product is chromatographed on silica gel using EA/MeOH 10:1. Colorless oil.

$R_f(EA/MeOH 10:1)=0.14$ MS(FAB): 501 (M+1)

e) For the synthesis of the title compound of Example 3, 0.6 mmol of diacetonide 3d) is dissolved in 10 ml of MeOH together with 2.4mmol of p-toluene-sulfonic acid and the mixture is stirred at RT for 2 h. It is filtered through a basic ion exchanger and the solvent is removed in vacuo. Colorless, hygroscopic oil.

$R_f$(Acetone/$H_2O$ 10:1)=0.09 MS(FAB): 421 (M+1) For storage, the product was converted into the hydrochloride. mp 188° C.

EXAMPLE 4

4-[2(S)-Hydroxypropylamino]-3-methylsulfonylbenzoylguanidine hydrochloride

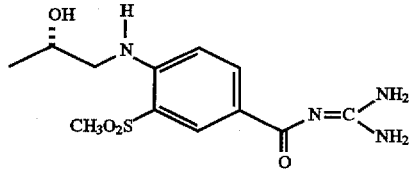

Synthesis route:

a) 4-[2(S)-Hydroxpropylamino]-3-methylsulfonylbenzoic acid 10 mmol of 2(S)-hydroxypropylamine are reacted with 4-fluoro-3-methylsulfonylbenzoic acid analogously to 3c). Brownish crystals.

mp 158° to 160° C. MS(DCI): 274 (M+1)

b) Methyl 4-[2(S)-hydroxypropylamino]-3-methylsulfonyl benzoate 7 mmol of benzoic acid 4a) are dissolved in 30 ml of MeOH together with 14 mmol $SOCl_2$ and the mixture is boiled under reflux for 3 h. The solvent is then removed in vacuo, the residue is taken up in 100 ml of EA and the solution is washed 3 times with 50 ml of $Na_2CO_3$ solution each time. It is dried over $Na_2SO_4$, the solvent is removed in vacuo, and the residue is then recrystallized from EA/HEP.

mp 95° C.

$R_f(MTB)=0.30$ MS(DCI): 288 c) For the synthesis of the title compound of Example 4, 5 mmol of the methyl ester 4b) are reacted according to general procedure B and chromatographed on silica gel using EA/MeOH 5:1.

mp 136° to 140° C. $R_f(EA/MeOH 5:1)=0.14$ Conversion to the hydrochloride gave colorless crystals.

mp 240° C. MS(DCI): 315 (M+1)

The title compound of Example 5 was synthesized analogously to Example 4:

EXAMPLE 5

4-[2(R)-Hydroxypropylamino]-3-methylsulfonylbenzoylguanidine hydrochloride

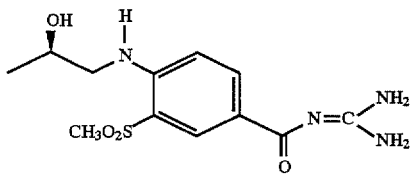

mp 203° C. MS (DCl): 315 (M+1)

EXAMPLE 6

3-Methylsulfonyl-4-[2(R,S),3-dihydroxypropyl]thiobenzoylguanidine

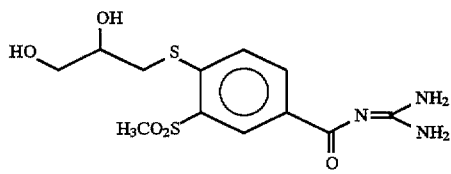

a) Methyl 3-methylsulfonyl-4-[2(R,S),3-dihydroxypropyl]thiobenzoate 20 mmol of methyl 4-chloro-3-methylsulfonylbenzoate, 20 mmol of 1-thioglycerol and 60 mmol of $K_2CO_3$ (anhydrous) are stirred for 24 h at RT in 70 ml of tetramethylurea. The reaction product is poured into 30 ml of $Na_2CO_3$ and extracted 3 times with 300 ml of EA. The extracts are dried over $Na_2SO_4$ and the solvents are removed in vacuo. Chromatography on silica gel using EA yields colorless crystals. mp≡136° C.

$R_f$ (EA)≡0.23 MS(DCl): 321 (M+1)

b) 3-Methylsulfonyl-4-[2(R,S),3-dihydroxypropyl]thiobenzoylguanidine 5 mmol of methyl ester a) and 25 mmol of guanidine are heated under reflux for 6 h in 40 ml of THF (anhydrous). The mixture is poured into 100 ml of satd. $Na_2CO_3$ solution and extracted 3 times using 150 ml of EA. The extracts are dried over $Na_2SO_4$ and the solvent is removed in vacuo.

Chromatography on silica gel using EA/MeOH 3:1 yields the title compound of Example 6 as a colorless foam.

$R_f$ (EA/MeOH 3:1)≡0.23 MS(DCl): 348 (M+1)

EXAMPLE 7

3-Methylsulfonyl-4-[1'-oxo-2'-phenylethyl]benzoylguanidine hydrochloride

Colorless crystals, melting point 198° C.

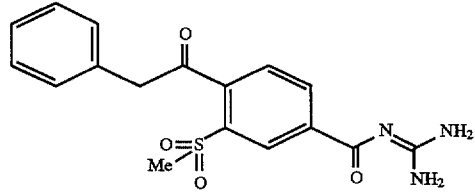

Synthesis route:

a) Methyl 3-methylsulfonyl-4-[(2'-phenyl)ethynyl]benzoate from methyl 4-bromo-3-methylsulfonylbenzoate by Stephans-Castro coupling with 2.5 equivalents of phenylacetylene, stirring at RT for 24 h in the presence of catalytic (5 mol %) bis(triphenylphosphine)palladium(II) chloride, 15 mol % of copper(I) iodide and 3 equivalents of n-butylamine in THF, aqueous ammonium chloride work-up, extraction with ethyl acetate and subsequent column chromatography on silica gel using ethyl acetate/cyclohexane (3:7), colorless crystals, melting point 138°–39° C.

b) Methyl 3-methylsulfonyl-4-[1'-oxo-2'-phenylethyl]benzoate from a) by treatment of the acetic acid solution with mercury(II) acetate in the presence of conc. sulfuric acid, and subsequent heating to 80° C. for 3 h. After filtration and dilution with water, the mixture is extracted with ethyl acetate, and the organic extract is washed with satd. $NaHCO_3$ solution until neutral and subjected to column chromatography using cyclohexane/ethyl acetate 1:1 as the eluent mixture. Colorless crystals, melting point 160°–161° C.

c) 3-Methylsulfonyl-4-[1'-oxo-2'-phenylethyl]benzoic acid from b) in methanol by hydrolysis with 1N NaOH at room temperature. Colorless crystals, melting point 229° C.

d) 3-Methylsulfonyl-4-[1'-oxo-2'-phenylethyl]benzoylguanidine hydrochloride from c) analogously to variant A.

EXAMPLE 8

4-[2'-Cyclohexyl-1'oxo-ethyl]3-methylsulfonylbenzoylguanidine hydrochloride

Colorless crystals, melting point 224°–25° C.

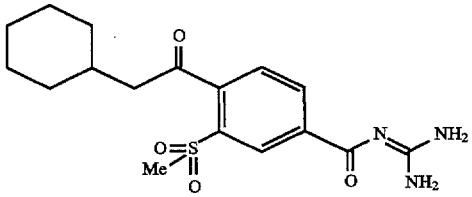

Synthesis route:

a) Methyl 4-[(2'-cyclohexyl)ethynyl]-3-methylsulfonylbenzoate from methyl 4-bromo-3-methylsulfonylbenzoate by Stephans-Castro coupling as described for 7a), coupling component cylcohexylacetylene, colorless crystals, m.p. 81°–82° C.

b) Methyl 3-methylsulfonyl-4-[2'-cyclohexyl-1'-oxoethyl]benzoate from 8a) analogously to 7b), colorless crystals, melting point 130°–131° C.

c) 3-Methylsulfonyl-4-[2'-cyclohexyl-1'-oxoethyl]benzoic acid from 8b) analogously to 7c), colorless crystals, melting point 174° C.

d) 4-[2'-Cyclohexyl-1'-oxoethyl]-3-methylsulfonylbenzoylguanidine hydrochloride from 8c) according to Variant A.

EXAMPLE 9

4-[1'-Hydroxy-2'-propyl]-3-methylsulfonylbenzoylguanidine hydrochloride

Colorless crystals, melting point 204°–6° C.

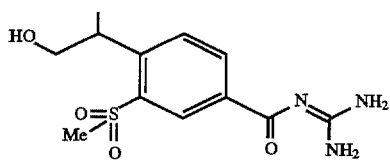

Synthesis route:
a) 4-[1'-Hydroxy-2'-propyl]-3-methylsulfonylbenzoic acid from methyl 4-isopropenyl-3-methylsulfonylbenzoate (see preliminary stage 2) by hydroboration using 0.35 equivalent of borane-dimethyl sulfide complex in THF with heating under reflux for 2 days. After rendering alkaline with 2N NaOH, the mixture is oxidized using 30% $H_2O_2$ solution. Aqueous work-up, extraction with ethyl acetate, evaporation and trituration with ether gives colorless crystals, melting point 187°–89° C.

b) Methyl 4-[1'-hydroxy-2'-propyl]-3-methylsulfonylbenzoate from 9a) using 1.2 equivalents of methyl iodide in the presence of potassium carbonate with heating for 3 hours under reflux. Aqueous work-up, column chromatography using cyclohexane/ethyl acetate 1:1. Colorless crystals, melting point 127°–29° C.

c) 4-[1'-Hydroxy-2'-propyl]-3-methylsulfonylbenzoylguanidine hydrochloride from 9b) analogously to Variant B.

Preliminary Stage 1
Isopropenylboronic acid 90 mmol of isopropenyl bromide and 99 mmol of Mg are reacted in 50 ml of diethyl ether to give the Grignard compound. This suspension is slowly added dropwise at –60° C. to a solution of 90 mmol of trimethyl borate in 100 ml of diethyl ether. The mixture is stirred at RT for 1 h, the solvent is removed in vacuo and 300 ml of 4N NaOH solution are added. The $Mg(OH)_2$ is then filtered off with suction and washed with 100 ml of $H_2O$, and the filtrate is extracted twice with 100 ml of DIP each time. The aqueous phase is then adjusted to pH=1 and extracted 4 times using 200 ml of EA each time. The EA phase is dried over $MgSO_4$ and the solvent is removed in vacuo. 2.0 g of an amorphous solid are obtained, which is further reacted without purification.

Preliminary Stage 2
Methyl 4-isopropenyl-3-methylsulfonylbenzoate 23 mmol of methyl 4-bromo-3-methylsulfonylbenzoate, 54 mmol of $Na_2CO_3$, 2.9 mmol of triphenylphosphine and 1.5 mmol of $Pd(OAc)_2$ are stirred intensively at RT for 5 min in 200 ml of toluene and 15 ml of $H_2O$. A solution of 23 mmol of boronic acid according to Preliminary Stage 1 is then added in 50 ml of EtOH and the mixture is boiled under reflux for 1.5 h. After phase separation, the organic phase is washed twice with 50 ml of NaCl solution and the aqueous phase is extracted twice with 100 ml of EA. The combined organic phases are dried over $Na_2SO_4$, the solvents are removed in vacuo and the residue is chromatographed on silica gel using DIP. 1.4 g of a colorless oil are obtained.

$R_f$(DIP)=0.46 MS(DCl): 255 (M+1)

EXAMPLE 10

4-[1'-Methoxy-2'-propyl]-3-methylsulfonylbenzoylguanidine hydrochloride

Colorless crystals, melting point 190° C.

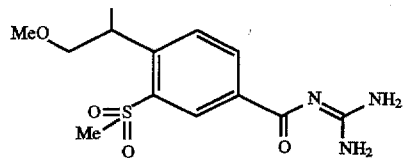

a) Methyl 4-[1'-Methoxy-2'-propyl]-3-methylsulfonylbenzoate from 9b using sodium hydride in the presence of 1.5 equivalents of methyl iodide by heating at 50° C. for 4 hours in THF. Aqueous work-up, column chromatographycyclohexane/ethyl acetate 8:2. Colorless crystals, amorph.

b) 4-[1'-Methoxy-2'-propyl]-3-methylsulfonylbenzoylguanidine hydrochloride from 10a) analogously to Variant B.

We claim:

1. A compound of formula I

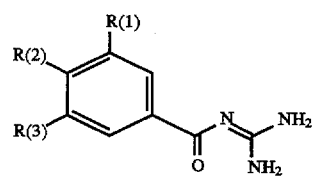

in which:
R(1)=—$CF_3$, R(4)—$SO_2$, or R(5)R(6)N—$SO_2$—, wherein
R(4) is ($C_1$–$C_4$)-alkyl, and
R(5) and R(6) are identical or different and are H or ($C_1$–$C_4$)-alkyl;
R(2)=—OR(10), —NHR(10), —NR(10)R(11), —CHR(10)R(12), —(C=O)—R(14), or

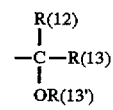

wherein R(10) and R(11) are identical or different and are —$(CH_2)_p$—$(CHOH)_q$—R(21) or —$(CH_2)_p$—O—$(CH_2$—$CH_2O)_q$—R(21),
wherein R(21) is hydrogen or methyl,
p is zero or 1, and q is 1, 2, 3, 4, or 5, R(12) and R(13) are identical or different and are hydrogen or $(C_1-C_6)$-alkyl, R(13') is hydrogen, R(14) is hydrogen, $(C_4-C_8)$-cycloalkyl or —R(15), wherein R(15) is phenyl, R(19) and R(20) are hydrogen or $(C_1-C_3)$-alkyl; and R(3) is hydrogen; or a pharmaceutically tolerable salt thereof.

2. A pharmaceutical composition for treating or preventing ischemic conditions of the heart, which comprises a pharmaceutically effective amount of a compound of formula I as claimed in claim 1 and a pharmaceutically acceptable auxiliary.

3. A method for treating or preventing ischemic conditions of the heart, which comprises administering to a host in need thereof an effective amount of a compound of formula I as claimed in claim 1.

* * * * *